(12) United States Patent
Tian

(10) Patent No.: US 9,180,087 B2
(45) Date of Patent: Nov. 10, 2015

(54) CHINESE MEDICINE HAIR-REGROWTH PREPARATION AND FORMULA AND PREPARATION METHOD THEREFOR

(75) Inventor: Zhiyuan Tian, Guangdong (CN)

(73) Assignee: Zhixian Yuan, Guangdong (CN)

( * ) Notice: Subject to any disclaimer, the term of this patent is extended or adjusted under 35 U.S.C. 154(b) by 397 days.

(21) Appl. No.: 13/811,666

(22) PCT Filed: Oct. 26, 2011

(86) PCT No.: PCT/CN2011/081336
§ 371 (c)(1),
(2), (4) Date: Jan. 23, 2013

(87) PCT Pub. No.: WO2012/059014
PCT Pub. Date: May 10, 2012

(65) Prior Publication Data
US 2013/0122109 A1    May 16, 2013

(30) Foreign Application Priority Data
Nov. 1, 2010   (CN) .......................... 2010 1 0532862

(51) Int. Cl.
| | | |
|---|---|---|
| A61K 36/00 | (2006.01) |
| A61K 36/268 | (2006.01) |
| A61K 36/481 | (2006.01) |
| A61K 36/704 | (2006.01) |
| A61K 36/232 | (2006.01) |
| A61K 36/236 | (2006.01) |
| A61K 36/537 | (2006.01) |
| A61K 36/736 | (2006.01) |
| A61K 36/52 | (2006.01) |
| A61K 36/605 | (2006.01) |
| A61K 8/98 | (2006.01) |
| A61K 9/00 | (2006.01) |
| A61K 9/06 | (2006.01) |
| A61K 35/57 | (2015.01) |
| A61K 36/185 | (2006.01) |
| A61K 36/21 | (2006.01) |
| A61K 36/47 | (2006.01) |
| A61K 36/9068 | (2006.01) |
| A61Q 7/00 | (2006.01) |
| A61K 8/92 | (2006.01) |
| A61K 8/97 | (2006.01) |
| A61K 8/34 | (2006.01) |
| A61K 35/64 | (2015.01) |

(52) U.S. Cl.
CPC . *A61K 8/981* (2013.01); *A61K 8/34* (2013.01); *A61K 8/925* (2013.01); *A61K 8/97* (2013.01); *A61K 9/0014* (2013.01); *A61K 9/06* (2013.01); *A61K 35/57* (2013.01); *A61K 35/64* (2013.01); *A61K 36/185* (2013.01); *A61K 36/21* (2013.01); *A61K 36/232* (2013.01); *A61K 36/236* (2013.01); *A61K 36/47* (2013.01); *A61K 36/481* (2013.01); *A61K 36/537* (2013.01); *A61K 36/704* (2013.01); *A61K 36/736* (2013.01); *A61K 36/9068* (2013.01); *A61Q 7/00* (2013.01)

(58) Field of Classification Search
None
See application file for complete search history.

(56) References Cited

FOREIGN PATENT DOCUMENTS

| CN | 1879595 A | 12/2006 |
| CN | 1895212 A | 1/2007 |
| CN | 101485831 A | 7/2009 |
| CN | 102000311 A | 4/2011 |

*Primary Examiner* — Qiuwen Mi

(57) ABSTRACT

A formula of Chinese Materia Medica preparation beneficial for hair growth contains ginger, *Astragalus Mongholicus*, *Polygonum Multiflorum*, black ants, *Angelica Sinensis*, *Alternanthera Sessilis*, *Ligusticum Wallichii*, *Salviae Miltiorrhizae*, dodder seeds, almonds, black soybean, walnuts, feather cockscomb seeds, Cortex Lycii Radicis, *Eclipta Alba*, mulberry, internal fats from a silkie and duck, and ethanol solution. A method for preparing the formula is also provided.

4 Claims, No Drawings

CHINESE MEDICINE HAIR-REGROWTH PREPARATION AND FORMULA AND PREPARATION METHOD THEREFOR

BACKGROUND OF THE INVENTION

The invention refers to a Chinese material medica preparation beneficial for hair growth, and to be specific, the invention is related to a formula and preparation method of Chinese meteria medica preparation provided with a function of hair growth.

With a high efficient and fast-paced way of life in modern city, more and more people begin to lose their hair. Worse still, this phenomenon even become increasingly serious especially among young people for they usually have to be concerned about the early shedding black hair. Currently, though there are many pharmaceutical preparations for treating lipsotrichia in the market, as regard to the western medicine, firstly it is relatively expensive for the patients have to continuously receive several courses of treatment, which will increase a heavy economic burden for the patients and secondly, the bodies of patients will suffer from a certain side effect due to the long time use of medication. As to the pure traditional Chinese medicine in the market it has a slow efficacy and instability. Thus although it can temporarily support the growth of a part of hair due to the stimulation of hair follicle of head the new small hair will easily get shedding once stop using medication. The main reason is that the pathological changes of hair follicle are related to the lack of nutrition of hair growth environment. Therefore, patients need a medication with a good efficacy, continuous hair growth and a relatively inexpensive price to tackle the mentioned problem.

BRIEF SUMMARY OF THE INVENTION

The invention is aimed to offer a composition of Chinese materia medica beneficial for hair growth and to be specific to offer a composition of Chinese materia materia and its method of preparation beneficial for hair growth by combining modern Chinese and western medicine technology, on the basis of the secret prescription handed down from the ancestors and according to the deficiencies of the above present technology. The preparation made by the invention can be applied to various hair scalps without any anaphylaxis and non-toxic side effect after using it to clean hair, which enables medicine to penetrate into skin quickly and achieve the goal of hair growth with a quick and good effect in hair growth, low cost and a simple and feasible preparation process.

The technical plan of the invention is as follows:

The invention is a thick paste composition which is prepared by mixing ginger, *astragalus mongholicus, polygonum multiflorum*, black ants, *angelica sinensis, alternanthera sessilis, ligusticum wallichii, salviae miltiorrhizae*, dodder seed, almonds, black soya bean, walnuts, the seed of feather cockscomb, cortex lycii radicis, *eclipta alba*, mulberry, fat extract of silkie and duck, in addition, 65% ethanol solution and 40% ethanol solution.

Wherein the quality of each composition is:
Ginger 55-100 g
*Astragalus mongholicus* 75-100 g
*Polygonum multiflorum* 100-150 g
Black ants 80-90 g
*Angelica sinensis* 60-120 g
*Alternanthera sessilis* 85-125 g
*Ligusticum wallichii* 60-80 g
*Salviae miltiorrhizae* 75-95 g
Dodder seed 40-50 g
Almonds 60-100 g
Black soya bean 100-120 g
Walnuts 50-80 g
The seed of feather cockscomb 62-80 g
Cortex lycii radicis 30-40 g
*Eclipta alba* 40-80 g
Mulberry 60-80 g,
A silkie,
A duck.
In addition,
65% Ethanol solution 2000-3000 g 40% Ethanol solution 2800-3500 g.

In order to obtain a better effect, the quality of raw material of the invention can be optimized as follows:
Ginger 60-80 g
*Astragalus mongholicus* 80-90 g
*Polygonum multiflorum* 100-120 g
Black ants 80-90 g
*Angelica sinensis* 60-100 g
*Alternanthera sessilis* 90-100 g
*Ligusticum wallichii* 70-80 g
*Salviae miltiorrhizae* 80-90 g
Dodder seed 40-50 g
Almonds 80-100 g
Black soya bean 100-120 g
Walnuts 70-80 g
The seed of feather cockscomb 70-80 g
Cortex lycii radicis 30-40 g
Mulberry 60-80 g,
A silkie,
A duck.
In addition,
65% Ethanol solution 2000-2500 g 40% Ethanol solution 2800-3000 g.

Of course, in order to obtain further better effect, the quality of the raw material of the invention can still be optimized as follows:
Ginger 80 g
*Astragalus mongholicus* 90 g
*Polygonum multiflorum* 100 g
Black ants 90 g
*Angelica sinensis* 100 g
*Alternanthera sessilis* 90 g
*Ligusticum wallichii* 80 g
*Salviae miltiorrhizae* 85 g
Dodder seed 45 g
Almonds 85 g
Black soya bean 105 g
Walnuts 75 g
The seed of feather cockscomb 80 g
Cortex lycii radicis 40 g
*Eclipta alba* 60 g
Mulberry 80 g
A silkie,
A duck.
In addition,
65% Ethanol solution 2000 g 40% Ethanol solution 2800 g.

The mentioned method of preparation of Chinese material medica beneficial for hair growth includes the following steps:

1). Prepare the Chinese material medica formula mixed with ginger, *astragalus mongholicus, polygonum multiflorum*, black ants, *angelica sinensis, alternanthera sessilis, ligusticum wallichii, salviae miltiorrhizae* and dodder seed in proportion and put it at a high temperature of 50-70° C. for drying and then cool it down naturally to the room temperature;

2). Put the above Chinese material medica formula into the grinder for grinding and then reserve as powder after a 80 mesh sieve;

3). Prepare the Chinese material medica formula mixed with almonds, black soya bean, walnuts, the seed of feather cockscomb, cortex lycii radicis, *eclipta alba* and mulberry in proportion and put it at a high temperature of 70-80° C. for drying and then cool it down naturally to the room temperature;

4). Put the above traditional Chinese medicine formula into the grinder for grinding and then reserve as powder after a 80 mesh sieve;

5). Take out 200 g of internal fats of each silkie and duck after slaughtered and put them into a clean bowl and then add 20 ml water into the bowl so as to put them into the pot for 10 minutes' steaming and reserve fresh oil after filtration.

6). Put the composition obtained from the second step into 40% ethanol solution which is equivalent to 2 times of the original amount for 3-5 days' soakage and then release the soakage solution for reservation;

7). Then put the above soaked residue of composition into 65% ethanol solution that is equivalent to 1.5 times of the original amount for 3 days' soakage and release the soakage solution for use;

8). Combine and filtrate the above two soakage solutions and concentrate the solutions into a thick paste with a proportion of 1.28-1.3 for use after retrieving ethanol solution;

9). Put the composition prepared by the fourth step into the 40% ethanol solution that is equivalent to 2 times of quality of the original amount for 5 days' soakage and then release and filtrate the soakage solution for use;

10). Then put the above soaked residue of composition into 40% ethanol solution that is equivalent to 2 times of the original amount for 5 days' soakage, then release and filtrate the soakage solution for use;

11). Combine and filtrate the above two soakage solutions and concentrate the solutions into a thick paste with a proportion of 1.28-1.3 for use after retrieving ethanol solution;

12). Mix the thick paste compositions prepared by the eighth and eleventh steps, add the fresh fat oil of silkie and duck obtained from the fifth step, then stir evenly, package and sterilize the above mixture and such Chinese materia medica preparation can be obtained.

When you use the above preparation you can take a proper amount of it and put it on your head. After that, please wipe and massage your scalp as well as wash your hair with clean water. If you use it for a long-time you will receive a good effect, which will enable small hair to grow rapidly and maintain the medical efficacy.

There are various Chinese material medica related to hair growth and hair breeding in the herbal documents of ancient China, among which many of them have been verified with a good efficacy by modern medicine. No matter people in the foreign countries or those in China pay highly attention to the hair growth and hair breeding of Chinese material medica. In the invention, Silkie is mild in property and sweet in taste without toxicity and can penetrate into liver and kidney meridians. With rich vitamin, trace element, protein and 18 amino acids it has the efficacy of nourishing Yin and removing heat, nourishing liver and kidney and nourishing Qi and blood, which can promote hair growth and is beneficial for the nourishment of scalp and protection of hair.

*Astragalus mongholicus* contains various amino acid, betaine, folic acid, alkaloid and trace element needed for human body and it is conducive to expand blood vessels, improve nutrition of skin and prevent the generation of yellow hair and white hair.

*Polygonum multiflorum* contains nutritious ingredients of lecithin and has the efficacy of nourishing blood and expelling wetness, regulating nervus and incretion, providing nutrition for hair root, enhancing the generation of hair melanin and making hair become blacker. At the same time, it still contains chrysophanol and a great deal of starch. The glucose generated by the hydrolysis of starch can provide nourishment for hair and is also the best raw material of Chinese material medica used for the preparation of hair conditioning agent. According to the experimental demonstration of modern pharmacology, lecithin contained in *polygonum multiforum* is an important raw material of cell membrane, which can promote the metabolism and growth and development of cells, delay senium of cells and prolong life.

Black ant consists of glyceride, lecithin, calcium, phosphorus and ferrum. Wherein the content of ferrum in black ant ranks in the front of various other medicines and it is able to enrich blood, moisten the skin and nourish hair. In addition, it is an ideal roborant for the nourishment of liver and kidney and the five internal organs and can be used to treat the symptom of early white hair and anemia of hair as well as yellow hair. Moreover, it is beneficial to treat lipsotrichia and promote the growth of hair and has become one of the commonly used medicines among the formula of cosmetology and hairdressing.

*Angelica sinensis* can promote the circulation of blood, enrich blood and relieve pain and moisten skin. In addition, it is still able to expand blood capillary of scalp and skin, promote the circulation of blood and prevent the shortage of vitamin E. *Angelica sinensis* shampoo made from *angelica sinensis* extract can prevent lipsotrichia, moisten skin and hair and bring you a shinny black hair as well as prevent hair becoming yellow and white.

*Alternanthera sessilis* contains vitamin A1, B2 and C necessary to cosmetology and trace elements such as calcium, phosphorus and ferrumm, among which the contents of vitamin A and C are the highest. If extract of *alternanthera sessilis* is added into cosmetics, it can prevent lipsotrichia, bring you a shinny and black hair and has a notable efficacy on treating yellow and white hair, pale complexion and dry skin caused by the lack of vitamin and trace element necessary to the body. Due to the fact that it can still promote the generation of melanin of hair thus it has a good efficacy on the treatment of alopecia areata.

*Ligusticum wallichii* has a good effect on dispelling wind, invigorating the circulation of blood, moistening skin and relieving itching, which is beneficial for the improvement of facial nutrition. It has been testified by modern pharmacology that *ligusticum wallichii* can expand blood capillary of head, boost blood circulation, increase nutrition of hair and make hair become more flexible and hardened. Moreover, it is still able to delay the growth of white hair and maintain the smooth and luster of hair.

*Salviae miltiorrhizae* is a labiate plant which is slightly cold in property and bitter in taste. Its chemical constituent includes tanshinone I, II A and II B, isotanshinone I and IIA, cryptotanshinone, isocryptotanshinone, methylation of tanshinone and hydroxyl of tanshinone. The main efficacy of *salviae miltiorrhizae* is to invigorate the circulation of blood and remove stasis. Since it contains rich vitamin and trace element of zinc, cooper and ferrum, it can promote the generation of melanin of hair and improve the symptom of white and yellow hair and dried hair caused by the lack of trace element. Meanwhile, because *salviae miltiorrhizae* itself is red thus its red alkannin will be dissolved into oil after stewed. Thus it can be used for makeup and cosmetics and added into various maquillages or applied to other natural medicines, which has a variety of functions such as relieving itching, getting rid of dandruff, preventing and treating lipsotrichia, promoting hair growth, moistening hair and enhance the elasticity of skin.

*Polygonum multiflorum* is a root tuber of polygonaceae *polygonum* plants with a mild property and a bitter and puckery taste. Its chemical constituent contains lecithin emodin, chryso-phanol, rhein and physcion etc. Lecithin can be found in the root tuber of *polygonum multiflorum* and it is a main ingredient of nervous tissue, especially myelencephalon and meanwhile is an important raw material of blood cell and other cell membranes. It can promote the rebirth and development of blood cells. The people with lipsotrichia and white hair usually fail to provide adequate blood and nourishment for their hair. *Polygonum multiflorum* can nourish the blood of liver and kidney and can receive a better effect on treating white hair and lipsotrichia, especially for seborrheic lipsotrichia.

At the same time, ethanol solution can be used as surface active agent strengthening recuperation and combining with calcium and magnesium ion in the water to further enhance the elasticity and luster of hair and make hair become loose and easily to be combed.

Clinical Experiment 1:

1). Time of observation: Under the circumstances that the technical plan of the invention has not been disclosed, the six month from February of 2009 to July of 2009 are chosen as the time of observation.

2) Object of observation: Select 40 cases of illnesses: 20 cases for male and 20 cases for female; age: 18 cases for 16 to 25 years old and 22 cases for 25 to 35 years old; occupation: 10 cases of students and 10 cases of workers, 5 cases of farmers, 10 cases of teachers and 5 cases for others. Course of disease: from the time of paroxysm to time of treatment, 20 cases within 2 years, 10 cases from 2 years to 4 years and 10 cases of more than 4 years.

3). Method of use: use the shampoo made from the preparation of the invention to wash hair 3 times a day and the above procedure should be done after 1 hour's dinner each time; 1 month is equivalent to 1 course of treatment thus 6 courses of treatment are regarded as the observation of treatment efficacy.

4). Observation of effect:

The standard of effect is divided into: remarkableness, which means lipsotrichia is not obvious with grown small hair of more than 10%; effectiveness, which means small hair has grown to more than 5% and lipsotrichia has also been controlled; invalidity, which means lipsotrichia has not been improved or alleviated basically.

Out of 40 cases of the results, there are 20 cases of remarkableness, 13 cases of effectiveness and 7 cases of invalidity and the total effective rate is 82.5%.

Clinical Experiment 2:

1). Time of observation: Under the circumstances that the technical plan of the invention has not been disclosed, the six month from January of 2008 to June of 2008 are chosen as the time of observation.

2). Object of observation: Select 20 cases of illnesses: 10 cases for male and 10 cases for female; age: 8 cases for 16 to 25 years old and 12 cases for 25 to 35 years old; occupation: 10 cases of students and 2 cases of workers, 2 cases of farmers, 2 cases of teachers and 4 cases for others. Course of disease: from the time of paroxysm to time of treatment, 10 cases within 2 years, 5 cases from 2 years to 4 years and 5 cases of more than 4 years.

3). Method of use: use the shampoo made from the preparation of the invention to wash hair 3 times a day and the above procedure should be done after 1 hour's dinner each time; 1 month is equivalent to 1 course of treatment thus 6 courses of treatment are regarded as the observation of treatment efficacy.

4). Observation of effect:

The standard of effect is divided into: remarkableness, which means lipsotrichia is not obvious with grown small hair of more than 10%; effectiveness, which means small hair has grown to more than 5% and lipsotrichia has also been controlled; invalidity, which means lipsotrichia has not been improved or alleviated basically.

Out of 20 cases of the results, there are 14 cases of remarkableness, 2 cases of effectiveness and 4 cases of invalidity and the total effective rate is 80%.

Through combining the above clinical data and the theoretical evidence of the invention, the beneficial effect of the invention lies in: the preparation of the invention can be applied to various hair and scalps without any anaphylaxis and non-toxic side effect after using it to clean hair, which enables medicine to penetrate into skin quickly and achieve the goal of hair growth with a quick and good effect in hair growth, low cost and a simple and feasible preparation process.

DETAILED DESCRIPTION OF THE INVENTION

The invention will be given further detailed explanation by combining the following implementation examples:

Implementation Example 1

The quality of raw material of the invention can be optimized as follows (g):

Ginger 100 g
*Astragalus mongholicus* 100 g
*Polygonum multiflorum* 150 g
Black ants 80 g
*Angelica sinensis* 60 g
*Alternanthera sessilis* 85 g
*Ligusticum wallichii* 60 g
*Salviae miltiorrhizae* 95 g
Dodder seed 50 g
Almonds 60 g
Black soya bean 120 g
Walnuts 80 g
The seed of feather cockscomb 80 g
Cortex lycii radicis 40 g
*Eclipta alba* 40 g
Mulberry 60 g,
A silkie,
A duck.
In addition,
65% Ethanol solution 2000 g 40% Ethanol solution 3000 g.

The mentioned method of preparation of hair growth and hair breeding includes the following steps:

1). Prepare the Chinese material medica formula mixed with ginger, *astragalus mongholicus, polygonum multiflorum*, black ants, *angelica sinensis, alternanthera sessilis, ligusticum wallichii, salviae miltiorrhizae* and dodder seed in proportion and put it at a high temperature of 50-70° C. for drying and then cool it down naturally to the room temperature;

2). Put the above Chinese material medica formula into the grinder for grinding and then reserve as powder after a 80 mesh sieve;

3). Prepare the Chinese material medica formula mixed with almonds, black soya bean, walnuts, the seed of feather cockscomb, cortex lycii radicis, *eclipta alba* and mulberry in proportion and put it at a high temperature of 70-80° C. for drying and then cool it down naturally to the room temperature;

4). Put the above traditional Chinese medicine formula into the grinder for grinding and then reserve as powder after a 80 mesh sieve;

5). Take out 200 g of internal fats of each silkie and duck after slaughtered and put them into a clean bowl and then add 20 ml water into the bowl so as to put them into the pot for 10 minutes' steaming and reserve fresh oil after filtration.

6). Put the composition obtained from the second step into 40% ethanol solution which is equivalent to 2 times of quality of the original amount for 3-5 days' soakage and then release the soakage solution for reservation;

7). Then put the above soaked residue of composition into 65% ethanol solution that is equivalent to 1.5 times of the original amount for 3 days' soakage and release the soakage solution for use;

8). Combine and filtrate the above two soakage solutions and concentrate the solutions into a thick paste with a proportion of 1.28-1.3 for use after retrieving ethanol solution;

9). Put the composition prepared by the fourth step into the 40% ethanol solution that is equivalent to 2 times of quality of the original amount for 5 days' soakage and then release and filtrate the soakage solution for use;

10). Then put the above soaked residue of composition into 40% ethanol solution that is equivalent to 2 times of the original amount for 5 days' soakage, then release and filtrate the soakage solution for use;

11). Combine and filtrate the above two soakage solutions and concentrate the solutions into a thick paste with a proportion of 1.28-1.3 for use after retrieving ethanol solution;

12). Mix the thick paste compositions prepared by the eighth and eleventh steps, add the fresh fat oil of silkie and duck obtained from the fifth step, then stir evenly, package and sterilize the above mixture and such a Chinese materia medica preparation can be obtained.

Implementation Example 2

The quality of raw material of the invention can still be optimized as follows (g):
Ginger 65 g
*Astragalus mongholicus* 85 g
*Polygonum multiflorum* 110 g
Black ants 90 g
*Angelica sinensis* 65 g
*Alternanthera sessilis* 95 g
*Ligusticum wallichii* 75 g
*Salviae miltiorrhizae* 85 g
Dodder seed 50 g
Almonds 85 g
Black soya bean 105 g
Walnuts 75 g
The seed of feather cockscomb 80 g
Cortex lycii radicis 35 g
*Eclipta alba* 45 g
Mulberry 70 g,
A silkie,
A duck.
In addition,
65% Ethanol solution 2000 g 40% Ethanol solution 2800 g
The method of preparation is the same as implementation 1.

Implementation Example 3

Wherein the quality of each composition is (g):
Ginger 80 g
*Astragalus mongholicus* 90 g
*Polygonum multiflorum* 100 g
Black ants 90 g
*Angelica sinensis* 100 g
*Alternanthera sessilis* 90 g
*Ligusticum wallichii* 80 g
*Salviae miltiorrhizae* 85 g
Dodder seed 45 g
Almonds 85 g
Black soya bean 105 g
Walnuts 75 g
The seed of feather cockscomb 80 g
Cortex lycii radicis 40 g
*Eclipta alba* 60 g
Mulberry 80 g,
A silkie,
A duck.
In addition,
65% Ethanol solution 2000 g 40% Ethanol solution 2800 g
The method of preparation is the same as implementation 1.

Implementation Example 4

Wherein the quality of each composition is (g):
Ginger 80 g
*Astragalus mongholicus* 93 g
*Polygonum multiflorum* 115 g
Black ants 88 g
*Angelica sinensis* 68 g
*Alternanthera sessilis* 88 g
*Ligusticum wallichii* 78 g
*Salviae miltiorrhizae* 78 g
Dodder seed 48 g
Almonds 60 g
Black soya bean 105 g
Walnuts 58 g
The seed of feather cockscomb 68 g
Cortex lycii radicis 38 g
*Eclipta alba* 48 g
Mulberry 68 g,
A silkie,
A duck.
In addition,
65% Ethanol solution 2000 g 40% Ethanol solution 2800 g
The method of preparation is the same as implementation 1.

The mentioned implementation examples are only several examples among the numerous modes of implementation of the invention. If the dose has been increased or reduced according to the proportion of technical plans in each formula, the treatment efficacy will not be influenced by the preparation and it should also be included within the right protection scope of the invention.

What is claimed is:
1. A formula of Chinese Materia Medica preparation beneficial for hair growth, in a form of a thick paste, said formula comprising 55-100 g of ginger, 75-100 g of *Astragalus Mongholicus,* 100-150 g of *Polygonum Multiflorum,* 80-90 g of black ants, 60-120 g of *Angelica Sinensis*, 85-125 g of *Alternanthera Sessilis*, 60-80 g of *Ligusticum Wallichii*, 75-95 g of *Salviae Miltiorrhizae*, 40-50 g of dodder seeds, 60-100 g of almonds, 100-120 g of black soybean, 50-80 g of walnuts, 62-80 g of feather cockscomb seeds, 30-40 g of Cortex Lycii Radicis, 40-80 g of *Eclipta Alba*, 60-80 g of mulberry, internal fats from a silkie and a duck, 2000-3000 g of 65% ethanol solution, and 2800-3500 g of 40% ethanol solution.

2. The formula according to claim 1, wherein a quantity of the ginger is 60-80 g, a quantity of the *Astragalus Mongholicus* is 80-90 g, a quantity of the *Polygonum Multiflorum* is 100-120 g, a quantity of the *Angelica Sinensis* is 60-100 g, a quantity of the *Alternanthera Sessilis* is 90-100 g, a quantity of the *Ligusticum Wallichii* is 70-80 g, a quantity of the *Salviae Miltiorrhizae* is 80-90 g a quantity of the dodder seeds is 40-50 g, a quantity of the almonds is 80-100 g, a quantity of the walnuts is 70-80 g, a quantity of the feather cockscomb seeds is 70-80 g, and a quantity of the *Eclipta Alba* is 40-60 g.

3. The formula according to claim 1, wherein a quantity of the ginger is 80 g, a quantity of the *Astragalus Mongholicus* is 90 g, a quantity of the *Polygonum Multiflorum* is 100 g, a quantity of the black ants is 90 g, a quantity of the *Angelica Sinensis* is 100 g, a quantity of the *Alternanthera Sessilis* is 90 g, a quantity of the *Ligusticum Wallichii* is 80 g, a quantity of the *Salviae Miltiorrhizae* is 85 g a quantity of the dodder seeds is 45 g, a quantity of the almonds is 85 g, a quantity of the black soybean is 105 g, a quantity of the walnuts is 75 g, a quantity of the feather cockscomb seeds is 80 g, a quantity of the Cortex Lycii Radicis is 40 g, and a quantity of the *Eclipta Alba* is 60 g, and a quantity of the mulberry is 80 g.

4. A method of preparing the formula of Chinese Materia Medica preparation beneficial for hair growth described in claim 1, wherein the method comprises the following steps:
 a) mixing 55-100 g of the ginger, 75-100 g of the *Astragalus Mongholicus*, 100-150 g of the *Polygonum Multiflorum*, 80-90 g of the black ants, 60-120 g of the *Angelica Sinensis*, 85-125 g of the *Alternanthera Sessilis*, 60-80 g of the *Ligusticum Wallichii*, 75-95 g of the *Salvia Miltiorrhizae* and 40-50 g of the dodder seeds to form a first mixture, drying the first mixture at a high temperature of 50-70° C., and then cooling down the first mixture to room temperature;
 b) grinding the first mixture to obtain first powders after passing a 80 mesh sieve;
 c) mixing 60-100 g of the almonds, 100-120 g of the black soybean, 50-80 g of the walnuts, 62-80 g of the feather cockscomb seeds, 30-40 g of the Cortex Lycii Radicis, 40-80 g of the *Eclipta Alba* and 60-80 g of the mulberry to form a second mixture, drying the second mixture at a high temperature of 70-80° C., and then cooling down the second mixture to room temperature;
 d) grinding the second mixture to obtain second powders after passing the 80 mesh sieve;
 e) taking out 200 g of the internal fats of each silkie and duck after slaughter, putting the internal fats into a clean bowl, adding 20 ml of water into the bowl, steaming the bowl in a pot for 10 minutes, and then obtaining fresh oil after filtration;
 f) adding the first powders from step b into the 40% ethanol solution having a mass 2 times a mass of the first powders from step b, immersing the first powders in the 40% ethanol solution for 3-5 days to obtain a first solution;
 g) adding residue of the first solution from step f into the 65% ethanol solution having a mass 1.5 times a mass of the residue of the first solution, immersing the residue of the first solution in the 65% ethanol solution for 3 days to obtain a second solution;
 h) combining the first solution of step f and the second solution of step g to obtain a combined solution, filtering the combined solution, recovering the 40% ethanol solution and the 65% ethanol solution used in steps f and g, and then concentrating the combined solution into a thick paste with a density of 1.28-1.3;
 i) adding the second powders from step d into the 40% ethanol solution having a mass 2 times a mass of the second powders; immersing the second powders in the 40% ethanol solution for 5 days to obtain a third solution, and then filtering the third solution;
 j) adding residue of the third solution from step l into the 40% ethanol solution having a mass 1.5 times a mass of the residue of the third solution, immersing the residue of the third solution in the 40% ethanol solution for 5 days to obtain a fourth solution, and then filtering the fourth solution;
 k) combining the third solution from step i and the fourth solution in step i to obtain a second combined solution, filtering the second combined solution, recovering the 40% ethanol solution used in steps i and j, and then concentrating the second combined solution into another thick paste with a density of 1.28-1.3;
 l) mixing the thick paste from step h and the thick paste from step k to obtain a mixed paste, adding the fresh oil obtained from step e into the mixed paste, stirring the mixed paste evenly, and then packaging and sterilizing the mixed paste to obtain the formula.

\* \* \* \* \*